(12) United States Patent
Inada et al.

(10) Patent No.: US 6,797,256 B2
(45) Date of Patent: Sep. 28, 2004

(54) COMPOSITION FOR DETERMINING PYRIMIDINE METABOLIZING ACTIVITY

(75) Inventors: Makoto Inada, Tokushima-ken (JP); Nobuhiro Ikei, Tokushima (JP); Hideji Nonomura, Tokushima-ken (JP); Yasuo Irie, Woburn, MA (US)

(73) Assignee: Otsuka Pharmaceutical Co. Ltd., Tokyo-To (JP)

( * ) Notice: Subject to any disclaimer, the term of this patent is extended or adjusted under 35 U.S.C. 154(b) by 0 days.

(21) Appl. No.: 09/928,434

(22) Filed: Aug. 14, 2001

(65) Prior Publication Data

US 2002/0132283 A1 Sep. 19, 2002

(30) Foreign Application Priority Data

Mar. 13, 2001 (JP) ........................................ 2001-070828

(51) Int. Cl.$^7$ .......................... A61K 51/00; A61B 5/055
(52) U.S. Cl. .......................... 424/9.1; 424/9.2; 424/9.3; 424/1.81; 436/173
(58) Field of Search ........................ 424/9.1, 9.2, 1.81, 424/1.65, 1.73, 9.3; 436/173; 514/49, 50, 256; 534/767; 536/28.52, 28.55

(56) References Cited

U.S. PATENT DOCUMENTS

| | | | | |
|---|---|---|---|---|
| 4,328,229 A | * | 5/1982 | Fujii et al. .................. | 424/251 |
| 5,670,331 A | * | 9/1997 | el Kouni et al. .............. | 435/15 |
| 5,707,602 A | | 1/1998 | Klein ........................ | 424/1.17 |
| 5,944,670 A | * | 8/1999 | Katzman ..................... | 600/543 |
| 6,232,448 B1 | | 5/2001 | Yoshikubo et al. ..... | 530/388.26 |
| 6,355,416 B1 | * | 3/2002 | Abramson ..................... | 435/6 |

OTHER PUBLICATIONS

Triplett et al., Synthesis of carbon–13 labeled uracil . . . , Journal of Labelled Compounds and Radiopharmaceuticals, 14(1), pp. 35–41, 1978.*

Van Kuilenburg et al., Pitfalls in the diagnosis of patients with partial dihydropyrimidine dehydrogenase deficiency, Clinical Chemistry, 46:1, pp. 9–17, Jan. 2000.*

Creasey et al., "The metabolism of uracil–2–$^{14}$C and the granulocyte response to endotoxin as indicators of the toxicity produced in patients receiving 5–fluorouracil, " *Clinical Pharmacology and Therapeutics*, vol. 8, No. 2:273–282.

Fernandez–Salguero et al., "Correlation between catalytic activity and protein content for the polymorphically expressed dihydropyrimidine dehydrogenase in human lymphocytes," *Biochemical Pharmacology*, vol. 50, No. 7:1015–1020 (1995).

Fleming et al., "Correlation between Dihydropyrimidine Dehydrogenase Activity in Peripheral Mononuclear Cells and Systematic Clearance of Fluorouracil in Cancer Patients," *Cancer Research*, vol. 52:2899–2902 (May 15, 1999).

Johnson, et al., "Semi–automated radioassay for determination of dihydropyrimidine dehydrohenase (DPD) activity; Screening cancer patients for DPD deficiency, a condition associated with 5–fluorouracil toxicity," *Journal of Chromatography B*, vol. 696:183–191 (1997).

Sumi et al., "Automated screening system for purine and pyrimidine metabolism disorders using high–performance liquid chromatography," *Journal of Chromatography B*, vol. 672:233–239 (1995).

Sumi et al., "Possible prediction of adverse reactions to fluorouracil by the measurement of urinary dihydrothymine and thymine," *Int'l. Journal of Molecular Medicine*, vol. 2:477–482 (1998).

* cited by examiner

*Primary Examiner*—Michael G. Hartley
(74) *Attorney, Agent, or Firm*—Finnegan, Henderson, Farabow, Garrett & Dunner, L.L.P.

(57) ABSTRACT

The present invention provide a method for assessing the sensitivity to a pyrimidine drug such as 5-FU which is degraded in the pyrimidine metabolic pathway, specifically in vivo pyrimidine metabolizing activity, of an individual subject; and a preparation useful for the assessment. The present invention can be carried out by: administering a preparation comprising as an active ingredient a pyrimidine compound or its metabolite which acts as a substrate for a pyrimidine metabolizing enzyme, in which compound or metabolite at least one of C, O and N is labeled with an isotope; and assessing in vivo pyrimidine metabolizing activity based on the amount of excreted metabolite.

20 Claims, 3 Drawing Sheets

FIG. 1

| 5-FU | : 5-Fluorouracil |
| --- | --- |
| FDHU | : Fluorodihydrouracil |
| F-ß-UPA | : Fluoro-ß-ureidopropionic acid |
| F-ß-alanine | : Fluoro-ß-alanine |
| DPD | : Dihydropyrimidine dehydrogenase |
| DHPase | : Dihydropyrimidinase |
| ß-UPase | : ß-Ureidopropionase |

COMPOSITION FOR DETERMINING PYRIMIDINE METABOLIZING ACTIVITY

TECHNICAL FIELD

The present invention relates to a preparation useful for assessing and determining the sensitivity of an individual subject to pyrimidine drugs, such as 5-fluorouracil, which serve as an anticancer drug. More specifically, the present invention relates to a preparation for measuring in vivo activity of pyrimidine metabolizing enzymes that participate pyrimidine drug metabolism, with ease by utilizing the expired air or urine.

The present invention further relates to a method for measuring in vivo pyrimidine metabolizing activity with ease using the preparation, and a method for assessing pyrimidine metabolizing activity (pyrimidine drug sensitivity) in an individual subject.

The present invention also relates to a method for establishing a dosage regimen (formula, dose, dosing frequency, etc.) of a pyrimidine drug for an individual subject, wherein pyrimidine metabolizing activity in the subject is assessed using the preparation before administration of the drug.

BACKGROUND OF THE INVENTION

Among pyrimidine drugs, 5-fluorouracil (hereinafter sometimes referred to as "5-FU") and its derivatives (such as tegafur, carmofur and doxifluridine) are anticancer drugs most widely used at present. 5-FU is degraded and inactivated mainly in the liver, by the actions of pyrimidine metabolizing enzymes. Specifically stated, 5-FU is metabolized first into 5-fluoro dihydrouracil (hereinafter sometimes referred to as "FDHU") by the action of dihydropyrimidine dehydrogenase (hereinafter sometimes referred to as "DPD"), and then into fluoro-β-alanine by the action of dihydropyrimidinase (hereinafter sometimes referred to as "DHPase"), and thereafter excreted in the urine (see FIG. 1).

It is reported that about 80% of 5-FU administered is degraded by this metabolic system (Cancer (Phila), 68, 499–501, 1991), and that DPD is the ratelimiting enzyme in this metabolic system (Cancer Res., 47: 2203–2206, 1987). Accordingly, 5-FU administration to subjects with pyrimidine metabolic abnormalities such as DPD deficiency or DPD activity reduction is likely to result in abnormally high 5-FU concentration in blood, thus causing severe side effects (e.g., myelosuppression and digestive symptoms) (Cancer Inves. 11 (2): 239–240, 1993). DPD activity greatly varies from individual to individual, and is also different between the sexes (J. Clin. Oncol., 12:2248–2253, 1994; Adv. Exp. Med. Biol., 431:811–816, 1998). Thus, in Europe and America, there arises the necessity of diagnosing DPD deficiency and DPD activity reduction in individual subjects to prevent 5-FU side effects.

There is an established DPD deficiency diagnosis method, wherein DPD activity of peripheral blood mononuclear cells is measured (Cancer Res., 53:5433–5438, 1993; Phermacogenetics. 4:301–306. 1994; J. Inherited. Metab. Dis., 16:574–576, 1993). However, the method is not suitable for selecting subjects to be given 5-FU, since the method involves use of radioactive substances and complicated pretreatment.

Recent progresses in genetic analysis techniques have facilitated diagnosis of DPD gene deficiency. Further, a number of reports have been made on polymorphism of DPD gene, which may cause DPD activity reduction. However, the correlation between the DPD gene polymorphism and DPD activity has not been elucidated yet. Thus, it is extremely difficult to assess DPD activity, in particular the degree of DPD activity, at the genetic level.

In the present situation where 5-FU therapy has proved effective and is often enhanced by drugs that inhibit DPD activity, there is a demand for the development of a simple method for screening a subject for metabolic abnormalities before 5-FU therapy, to predict and prevent side effects of 5-FU therapy in subjects with pyrimidine metabolic abnormalities.

DISCLOSURE OF THE INVENTION

An object of the present invention is to provide a preparation useful for determining the sensitivity, specifically in vivo metabolizing activity, of an individual subject to 5-FU or like pyrimidine drugs to be degraded in the pyrimidine metabolic pathway. Another object of the invention is to provide a preparation for measuring in vivo pyrimidine metabolizing activity in an individual subject with ease, using the expired air or urine. A further object of the invention is to provide a method for measuring in vivo pyrimidine metabolizing activity in an individual subject with ease, using the preparation.

A further object of the invention is to provide a method for assessing in vivo pyrimidine metabolizing activity in an individual subject with ease using the preparation. A still further object of the invention is to provide a method for establishing a dosage regimen of a pyrimidine drug for an individual subject, wherein the sensitivity of the subject to the drug is assessed by the above assessing method before administration of the drug to determine the dosage regimen based on the sensitivity.

The present inventors conducted intense research, focusing their attention to metabolic kinetics wherein pyrimidine compounds, which act as substrates for pyrimidine metabolizing enzymes, are degraded in vivo by the action of these enzymes and partially excreted as $CO_2$ in the expired air, the remainder being excreted predominantly in the urine. As a result, they found that excretion behavior of the metabolites can be precisely measured by labeling the substrate with an isotope, and that the pyrimidine metabolizing activity of an individual subject can be easily assessed from the excretion behavior. The inventors further found that the method for assessing pyrimidine metabolizing activity is useful for assessing the sensitivity of an individual subject to 5-FU or other pyrimidine drugs (pyrimidine drug metabolic capacity) to predict side effects of pyrimidine drugs in subjects with pyrimidine metabolic abnormalities. The present invention has been accomplished based on these findings.

The present invention provides the preparations for determining pyrimidine metabolizing activity, described in the following items 1 to 6:

1. A preparation for determining pyrimidine metabolizing activity, comprising as an active ingredient a pyrimidine compound or its metabolite in which at least one of C, O and N is labeled with an isotope.

2. A preparation according to item 1, wherein the pyrimidine compound or its metabolite is a substrate for a pyrimidine metabolizing enzyme or a precursor of the substrate.

3. A preparation according to item 2, wherein the pyrimidine metabolizing enzyme is at least one member selected from the group consisting of dihydropyrimidine dehydrogenase, dihydropyrimidinase and β-ureidopropionase.

4. A preparation according to any one of items 1 to 3, wherein the pyrimidine compound or its metabolite is at least one member selected from the group consisting of 5-fluorouracil, uracil, thymine, 5-fluorodihydrouracil, dihydrouracil, dihydrothymine, fluoro-β-ureidopropionic acid, β-ureidopropionic acid, β-ureidoisobutyric acid, doxifluridine, tegafur and carmofur.

5. A preparation according to any one of items 1 to 4, wherein the pyrimidine compound or its metabolite is a compound at least one of C and O is labeled with an isotope, and wherein the pyrimidine compound or its metabolite is capable of producing isotope-labeled $CO_2$ in vivo after administration.

6. A preparation according to any one of items 1 to 5, wherein the isotope is at least one member selected from the group consisting of $^{13}C$ $^{14}C$ $^{18}O$ and $^{15}N$.

The present invention further provides the methods for determining pyrimidine metabolizing activity, described in the following items 7 to 10:

7. A method for determining pyrimidine metabolizing activity in an individual subject, comprising administering a preparation according to any one of items 1 to 6 to the subject, and measuring behavior of an isotope-labeled metabolite.

8. A method for determining pyrimidine metabolizing activity in an individual subject, comprising administering a preparation according to any one of items 1 to 6 to the subject, and measuring excretion behavior of an isotope-labeled metabolite excreted from the body.

9. A method for determining pyrimidine metabolizing activity in an individual subject, comprising administering a preparation according to any one of items 1 to 6 to the subject, and measuring behavior of isotope-labeled $CO_2$ excreted in the expired air.

10. A method according to any one of item 7 to 9, wherein the pyrimidine metabolizing activity to be determined is an activity of at least one pyrimidine metabolizing enzyme selected from the group consisting of dihydropyrimidine dehydrogenase, dihydropyrimidinase and β-ureidopropionase.

The present invention also provides the methods for assessing pyrimidine metabolizing activity in an individual subject, described in the following items 11 to 13:

11. A method for assessing pyrimidine metabolizing activity in an individual subject, comprising administering a preparation according to any one of items 1 to 6 to the subject, and measuring behavior of an isotope-labeled metabolite, and comparing the excretion behavior in the subject with behavior in a healthy subject.

12. A method for assessing pyrimidine metabolizing activity in an individual subject, comprising administering a preparation according to any one of items 1 to 6 to the subject, measuring excretion behavior of an isotope-labeled metabolite excreted from the body, and comparing the excretion behavior in the subject with excretion behavior in a healthy subject.

13. A method for assessing pyrimidine metabolizing activity in an individual subject, comprising administering a preparation according to any one of items 1 to 6 to the subject, measuring excretion behavior of isotope-labeled $CO_2$ excreted in the expired air, and comparing the $CO_2$ excretion behavior in the subject with $CO_2$ excretion behavior in a healthy subject.

Furthermore, the present invention provides the methods for establishing a dosage regimen of a pyrimidine drug, described in the following items 14 to 15:

14. A method for establishing a dosage regimen of a pyrimidine drug for an individual subject, comprising assessing pyrimidine metabolizing activity in the subject by the method according to any one of item 10 to 13 before administration of the drug, and determining the dosage regimen based on the pyrimidine metabolizing activity.

15. A method according to item 14, wherein the pyrimidine drug is at least one fluorouracil drug selected from the group consisting of 5-fluorouracil, tegafur, carmofur and doxifluridine.

BEST MODE FOR CARRYING OUT THE INVENTION (1) Preparation for Determining Pyrimidine Metabolizing Activity The preparation for determining pyrimidine metabolizing activity of the invention comprises, as an active ingredient, a pyrimidine compound or its metabolite in which at least one of C, O and N is labeled with an isotope.

The pyrimidine compound or its metabolite for use in the invention may be, for example, a compound which acts as a substrate for a pyrimidine metabolizing enzyme. Examples of pyrimidine metabolizing enzymes include a series of enzymes that participate in pyrimidine metabolism (pyrimidine degradation) in vivo. Specific examples of such enzymes include dihydropyrimidine dehydrogenase (DPD), dihydropyrimidinase (DHPase) and β-ureidopropionase.

Specific examples of pyrimidine compounds and their metabolites that act as substrates for these enzymes include uracil, thymine and their derivatives as substrates for DPD; dihydrouracil, dihydrothymine and their derivatives as substrates for DHPase; and β-ureidopropionic acid, β-ureidoisobutyric acid and their derivatives as substrates for β-ureidopropionase. The derivatives are not limited as long as they act as substrates for DPD, DHPase or β-ureidopropionase, and are degraded by these enzymes and further degraded in vivo into final metabolites to be excreted in the expired air or urine. Preferred are those having no adverse effects on a living body.

Useful pyrimidine compounds include, in addition to the pyrimidine compounds acting as direct substrates for the above pyrimidine metabolizing enzymes (hereinafter sometimes referred to as "substrate compounds"), compounds acting as indirect substrates for these enzymes, i.e., so-called precursors, which are metabolized or degraded in vivo into substrates for pyrimidine metabolizing enzymes. Examples of such precursors include prodrugs of pyrimidine compounds (substrate compounds). Specific examples of precursors include cytosine, 5-methylcytosine, tegafur, carmofur and doxifluridine.

The pyrimidine compound or its metabolite for use in the invention is characterized in that at least one of C, O and N in its molecule is labeled with an isotope. Specific examples of the isotope include $^{13}C$, $^{14}C$, $^{18}O$ and $^{15}N$. These isotopes may be used either singly or in combination. The isotope may be radioactive or non-radioactive, but non-radioactive $^{13}C$, $^{18}O$ or $^{15}N$ is preferred from the safety point of view.

The pyrimidine compound or its metabolite for use in the invention may have one of the above isotopes in the molecule or may have two or more isotopes of the same or different elements. Although not limitative, the pyrimidine compound or its metabolite is preferably labeled so that at least part (C or O) of $CO_2$ excreted as the final metabolite in the expired air is labeled with an isotope. Examples of such pyrimidine compounds include those having isotope-labeled C at the 2-position.

The method for labeling a pyrimidine compound or its metabolite with these isotopes is not limited and may be any known method (e.g., Sasaki, "5.1 Application of Stable Isotopes in Clinical Diagnosis": Kagaku no Ryoiki (Journal of Japanese Chemistry) 107, "Application of Stable Isotopes in Medicine, Pharmacy and Biology", pp. 149–163 (1975), Nankodo: Kajiwara, RADIOISOTOPES, 41, 45–48 (1992), etc.). Some pyrimidine compounds and their metabolites labeled with these isotopes are commercially available, and these commercial products are conveniently usable.

The preparation for determining pyrimidine metabolizing activity of the invention can be suitably used to measure in vivo pyrimidine metabolizing activity. Specifically stated, in vivo pyrimidine metabolizing activity can be determined by administering the preparation to a subject, and then measuring isotope-labeled $CO_2$ excreted in the expired air or an isotope-labeled metabolite excreted in the urine or a body fluid to analyse excretion behavior of these metabolites (excretion amount, excretion rate and change in the amount and rate). When the urine or body fluid is used as the measurement sample, pyrimidine compounds, their metabolites and further metabolites can be simultaneously analyzed by a combination of separation analysis techniques such as liquid chromatography and gas chromatography. The in vivo pyrimidine metabolizing activity can be determined and assessed based on the quantitative ratio of these compounds and metabolites.

The preparation of the invention may be in any form that is suitable for the purposes of the invention. Examples of suitable forms include injections, intravenous injections, suppositories, eye drops, nose drops and other non-oral forms; and solutions (including syrups), suspensions, emulsions, tablets (either uncoated or coated), capsules, pills, powders, granules and other oral forms.

The preparation of the invention may consist substantially of the isotope-labeled pyrimidine compound or metabolite as an active ingredient, but may further contain any carriers or additives generally used in this field, according to the form of the preparation, as long as they do not impair the actions and effects of the preparation of the invention.

Examples of carriers for use in tablets include lactose, saccharose, sodium chloride, glucose, urea, starches, calcium carbonate, kaolin, crystalline cellulose, silicic acid and like excipients; simple syrups, glucose solutions, starch solutions, gelatin solutions, carboxymethyl cellulose, shellac, methyl cellulose, potassium phosphate, polyvinyl pyrrolidone and like binders; dry starches, sodium alginate, agar powder, laminaran powder, sodium hydrogencarbonate, calcium carbonate, polyoxyethylene sorbitan fatty acid esters, sodium lauryl sulfate, stearic acid monoglyceride, starches, lactose and like disintegrators; saccharose, stearic acid, cacao butter, hydrogenated oils and like disintegration inhibitors; quaternary ammonium bases, sodium lauryl sulfate and like absorption accelerators; glycerin, starches and like humectants; starches, lactose, kaolin, bentonite, colloidal silicic acid and like adsorbents; and purified talc, stearate, boric acid powder, polyethylene glycol and like lubricants. Further, the tablets may be sugar-coated tablets, gelatin-coated tablets, film-coated tablets or like tablets with ordinary coatings, or double-layer tablets, multi-layer tablets.

Useful carriers for use in pills include, for example, glucose, lactose, starches, cacao butter, hydrogenated vegetable oils, kaolin, talc and like excipients, gum arabic powder, tragacanth powder, gelatin and like binders; and laminaran, agar and like disintegrators.

Capsules are prepared in a routine manner, by mixing the isotope-labeled pyrimidine compound or its metabolite with any of the above carriers and then filling the mixture into hardened gelatin capsules, soft capsules or the like.

Useful carriers for use in suppositories include, for example, polyethylene glycol, cacao butter, higher alcohols, esters of higher alcohols, gelatin and semisynthetic glyceride.

When the preparation of the invention is prepared in the form of an injection, the injection solution, emulsion or suspension is sterilized and preferably isotonic with blood. Useful diluents for preparation of the injection include, for example, water, ethyl alcohol, macrogol, propylene glycol, ethoxylated isostearyl alcohol, polyoxylated isostearyl alcohol and polyoxyethylene sorbitan fatty acid esters. The injection may contain sodium chloride, glucose or glycerin in an amount sufficient to make an isotonic solution. Also, an ordinary solubilizer, buffer, soothing agent or the like can be added to the injection.

Further, the preparation of the invention in any of the above forms may contain a color, preservative, flavor, odor improver, taste improver, sweetener, stabilizer and other pharmaceutically acceptable additives. The above carriers and additives may be used either singly or in combination.

Figure 1:
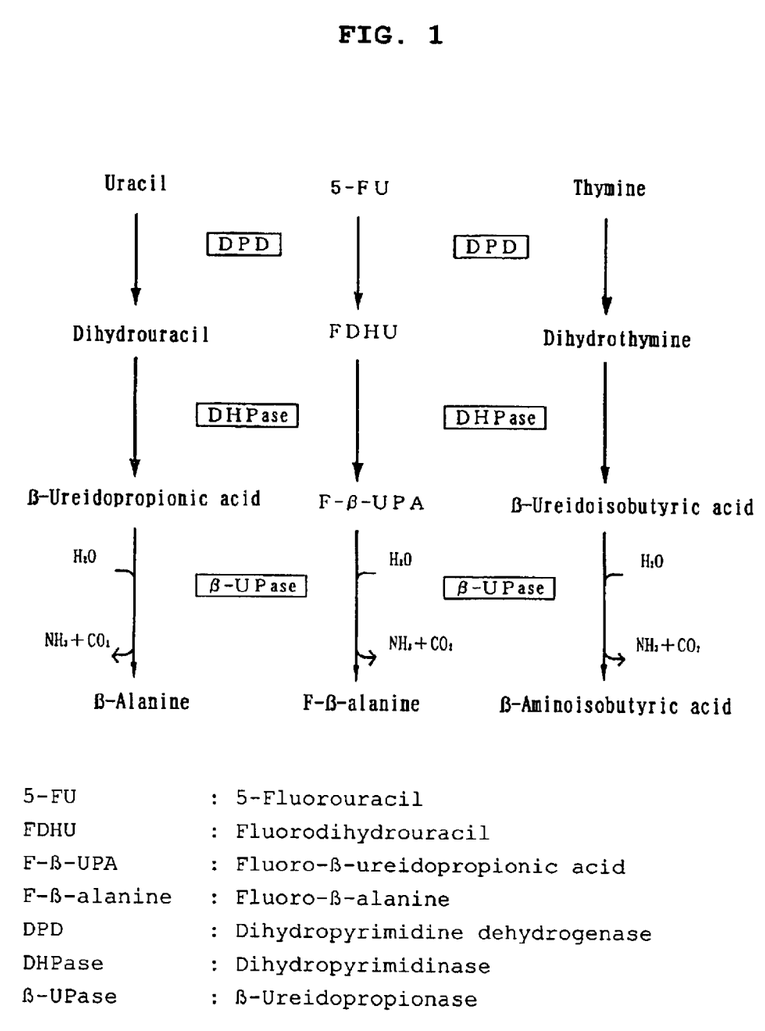
FIG. 1 shows the behavior of pyrimidine compounds (uracil, 5-fluorouracil (5-FU) and thymine) during metabolization by pyrimidine metabolizing enzymes (dihydropyrimidine dehydrogenase (DPD), dihydropyrimidinase (DHPase) and β-ureidopropionase (β-UPase)).

When the preparation of the invention is administered to a healthy subject in whom a series of pyrimidine metabolizing enzymes function normally, a pyrimidine compound or its metabolite contained as an active ingredient in the preparation is metabolically degraded as follows (see FIG. 1).

For example, when the preparation contains, as an active ingredient, uracil (or thymine) which acts as a substrate for DPD (the first enzyme in pyrimidine metabolism), the uracil (or thymine) is degraded in vivo into dihydrouracil (or dihydrothymine) by DPD, and then into β-ureidopropionic acid (or β-ureidoisobutyric acid) by DHPase (the second enzyme in pyrimidine metabolism), and further into $CO_2$ and β-alanine (or β-aminoisobutyric acid) by β-ureidopropionase (the third enzyme).

When the preparation contains, as an active ingredient, dihydrouracil (or dihydrothymine) which acts as a substrate for DHPase (the second enzyme in pyrimidine metabolism), the dihydrouracil (or dihydrothymine) is degraded in vivo into β-ureidopropionic acid (or β-ureidoisobutyric acid) by DHPase, and into $CO_2$ and β-alanine (or β-aminoisobutyric acid) by β-ureidopropionase (the third enzyme).

When the preparation contains, as an active ingredient, β-ureidopropionic acid (or β-ureidoisobutyric acid) which acts as a substrate for β-ureidopropionase (the third enzyme in pyrimidine metabolism), the β-ureidopropionic acid (or β-ureidoisobutyric acid) is degraded in vivo into $CO_2$ and β-alanine (or β-aminoisobutyric acid) by β-ureidopropionase.

The final metabolite $CO_2$ is excrete in the expired air, and the other final metabolite β-alanine (or β-aminoisobutyric acid) is excreted mainly in the urine. When excreted, at least one of the final metabolites ($CO_2$ and β-alanine or β-aminoisobutyric acid) is labeled with an isotope, according to the isotope-labeled site of the pyrimidine compound or its metabolite as an active ingredient. Therefore, the isotope label is used as an index to measure excretion behavior (excretion amount, excretion rate and change in the amount and rate) of the metabolite in a sample (the expired air when $CO_2$ is labeled, or the urine when β-alanine (or β-aminoisobutyric acid) is labeled). Based on the excretion behavior, in vivo pyrimidine metabolizing activity can be assessed. Further, the urine contains, in addition to the final metabolites, the administered compound such as a pyrimidine compound or its metabolite and/or metabolic intermediates of the administered compound, depending on the pyrimidine metabolizing activity of the individual subject. Thus, when the sample is the urine, it is preferred to use a combination of separation analysis techniques in order to simultaneously analyse the compounds contained in the sample. By such analysis, overall in vivo pyrimidine metabolizing activity can be assessed based on the quantitative ratio of these compounds in the sample.

The proportion of the isotope-labeled compound (active ingredient) in each dose of the preparation of the invention cannot be generally specified and is suitably selected, since the suitable proportion varies according to the types of sample and isotope-labeled compound. For example, when the preparation of the invention is designed to measure the amount of $^{13}CO_2$ excreted in the expired air using $^{13}C$-labeled uracil as the isotope-labeled compound, each dose of the preparation preferably contains 1 mg to 1 g, more preferably 10 to 100 mg, of $^{13}C$-labeled uracil.

(2) Method for Determining Pyrimidine Metabolizing Activity

The present invention also provides a method for determining in vivo pyrimidine metabolizing activity. The method can be carried out with ease, using the preparation for determining pyrimidine metabolizing activity of the invention described above.

Specifically stated, in vivo pyrimidine metabolizing activity can be determined as follows: the preparation of the invention is administered to an animal or human subject whose pyrimidine metabolizing activity is to be determined. Then, after a predetermined period of time, the expired air, urine, feces, blood, sweat or another body fluid is collected as an sample, and the amount of isotope-labeled metabolite excreted in the sample is measured and compared with the amount of isotope-labeled compound (pyrimidine compound or its metabolite) contained in the preparation administered.

The isotope-labeled compound in the sample can be measured and analyzed by a conventional analysis technique such as liquid scintillation counting, mass spectrography, infrared spectroscopy, emission spectral analysis or magnetic resonance spectral analysis, which is selected depending on whether the isotope used is radioactive or non-radioactive.

Pyrimidine metabolism (pyrimidine degradation) in vivo is effected by a series of pyrimidine metabolizing enzymes. Thus, a pyrimidine compound taken in the body is metabolically degraded mainly by the pyrimidine metabolizing enzymes and excreted from the body as $CO_2$ and other metabolites (e.g., β-alanine or its derivative). Of the metabolites, $CO_2$ is excreted primarily in the expired air, and other metabolites primarily in the urine.

The sample for use in the method of the invention can be selected according to the type of isotope-labeled metabolite produced depending on the isotope-labeled site in the administered pyrimidine compound or metabolite. Therefore, a suitable sample is the expired air when the isotope-labeled final metabolite is $CO_2$, and the urine when the final metabolite is β-alanine or another metabolite. The expired air is preferred from the viewpoint of ease of sample collection, and the urine is preferred from the viewpoint of feasibility of simultaneously analyzing a large number of metabolites.

The present invention further provides, as a preferred method for determining pyrimidine metabolizing activity, a method comprising administering the preparation for determining pyrimidine metabolizing activity to a subject, and measuring excretion behavior (such as excretion amount and excretion rate) of isotope-labeled $CO_2$ in the expired air.

This preferred method uses a preparation for determining pyrimidine metabolizing activity of the invention, which comprises, as an active ingredient, an isotope-labeled pyrimidine compound or metabolite designed to produce isotope-labeled $CO_2$ as a final metabolite. Specific examples of such isotope-labeled pyrimidine compounds include pyrimidine compounds having isotope-labeled C at the 2-position.

When $^{13}C$ is used as an isotope, the amount of $^{13}CO_2$ excreted in the expired air can be measured by a conventional technique for measuring $^{13}C$ in the expired air. Specifically stated, the preparation of the invention is administered to a subject, and the expired air is collected at intervals over time to measure the excretion behavior (excretion amount, excretion rate and change in the amount and rate) of $^{13}CO_2$ in the expired air, thereby determining and assessing in vivo metabolic activity toward the pyrimidine compound administered.

In the method for determining pyrimidine metabolizing activity of the invention, the total or individual activity of pyrimidine metabolizing enzymes participating in pyrimidine metabolism in vivo can be determined or assessed by selecting the active ingredient of the preparation for determining pyrimidine metabolizing activity.

For example, (i) in vivo activity of DPD can be mainly determined when using, as the active ingredient, uracil, thymine, a precursor thereof or like compound acting as a substrate for DPD, (ii) in vivo activity of DHPase can be mainly determined when using, as an active ingredient, dihydrouracil, dihydrothymine or like compound acting as a substrate for DHPase and (iii) in vivo activity of β-ureidopropionase can be mainly determined when using, as an active ingredient, β-ureidopropionic acid, β-ureidoisobutyric acid or like compound acting as a substrate for β-ureidopropionase. In vivo DPD activity can be satisfactorily assessed solely by (i), but for more precise assessment, the DHPase activity and β-ureidopropionase DPD activity determined by (ii) and (iii) may be taken into account for the DPD activity obtained by (i). Similarly, in vivo DHPase activity can be satisfactorily assessed only by (ii), but the β-ureidopropionase activity determined by (iii) can be taken into account for more precise assessment of DHPase activity.

When the sample is the urine, it is preferable to use a preparation comprising as an active ingredient a compound acting as a substrate for DPD, and measure the metabolites in the urine by a combination of separation techniques such as liquid chromatography and gas chromatography. This process can simultaneously separate and analyze pyrimidine compound metabolites excreted in the urine, and thus can determine and assess the total or individual activity of pyrimidine metabolizing enzymes from the quantitative ratio of the excreted metabolites or other factors.

The method for determining pyrimidine metabolizing activity of the invention can assess the total or individual activity of pyrimidine metabolizing enzymes in vivo. In this aspect, the present invention provides a method for assessing in vivo pyrimidine metabolizing activity in an individual subject.

In vivo pyrimidine metabolizing activity can be assessed by administering the preparation of the invention to a subject, measuring excretion behavior of isotope-labeled metabolite in the urine, the expired air or a body fluid such as blood, and comparing the excretion behavior in the subject with excretion behavior in a helthy subject.

Preferably, isotope-labeled $CO_2$ excretion behavior in the expired air of a subject is measured and compared with that of a healthy subject. In this method, excretion behavior (excretion amount, excretion rate and change in the amount and rate) of isotope-labeled $CO_2$ (e.g., $^{13}CO_2$) in the expired air can be determined and assessed by administering the preparation of the invention to a subject, measuring the proportion of $^{13}CO_2$ gas relative to carbon dioxide $^{12}CO_2$ excreted in the expired air ($^{13}CO_2/^{12}CO_2$ concentration ratio: $\delta^{13}C$ value) over time to find the carbon dioxide $\Delta$ value (‰), i.e., the difference in $\delta^{13}C$ value between before and after the administration of the preparation.

From the pyrimidine metabolizing activity in an individual subject assessed by the method of the invention, the sensitivity of the subject to the pyrimidine drug can be estimated. Therefore, the assessing method of the invention is useful for selecting a subject to whom a pyrimidine drug can be given, before administration of the drug.

Thus, the present invention provides a method for establishing a dosage regimen of a pyrimidine drug (formula (type and constitution of the drug), dose, dosing frequency, etc.) for a subject, comprising assessing pyrimidine metabolizing activity in the subject by the above assessing method before administration of the drug, and determining the dosage regimen based on the activity. Examples of pyrimidine drugs include those conventionally used as anticancer drugs, such as 5-fluorouracil, tegafur, carmofur, doxifluridine and like fluorouracil drugs.

The method of the invention is capable of assessing a subject's ability to degrade a pyrimidine drug in vivo beforehand, making it possible to predict and prevent side effects of pyrimidine drugs, particularly the above mentioned fluorouracil drugs, in subjects with pyrimidine metabolic abnormalities such as DPD deficiency and DPD activity reduction. Accordingly, the method of the invention is also useful as a method for screening a subject for the sensitivity to a fluorouracil drug before administration of the drug.

EXAMPLES

The following examples are provided to illustrate the present invention, and are not intended to limit the scope of the claims herein.

Example 1

Uracil having $^{13}C$-labeled carbon at the 2-position (uracil-2-$^{13}C$) was used as an isotope-labeled pyrimidine compound. An intravenous injection was prepared using uracil-2-$^{13}C$ as an active ingredient, and tested for usefulness for determining pyrimidine metabolizing activity.

(1) Preparation of a Preparation for Determining Pyrimidine Metabolizing Activity 300 mg of uracil-2-$^{13}C$ (Cambridge Isotope Laboratory) was dissolved in 24 ml of 0.1N NaOH/saline solution (measured out from 200 ml of 0.1N NaOH/saline solution prepared by diluting 2 ml of 10N sodium hydroxide solution with physiological saline), to give a preparation for determining pyrimidine metabolizing activity in the form of an injection (containing 50 mg of uracil-2-$^{13}C$ per 4 ml of the injection).

(2) Preparation of (E)-5-(2-Bromovinyl)-Uracil Preparation (E)-5-(2-bromovinyl)-uracil is a uracilantagonizing metabolic inhibitor which, in vivo, competes with uracil and acts as a substrate for dihydropyrimidine dehydrogenase (DPD) (Cancer Research 46, 1094–1101, March 1986, pp.1094–1101). 250 mg of (E)-5-(2-bromovinyl)uracil and 2.25 g of gum arabic were mixed, and the mixture was kneaded with a slight amount of water to prepare 45 ml of a suspension (containing 83.3 mg of (E)5-(2-bromovinyl)-uracil per 15 ml of the suspension).

(3) Experiment

Figure 2:
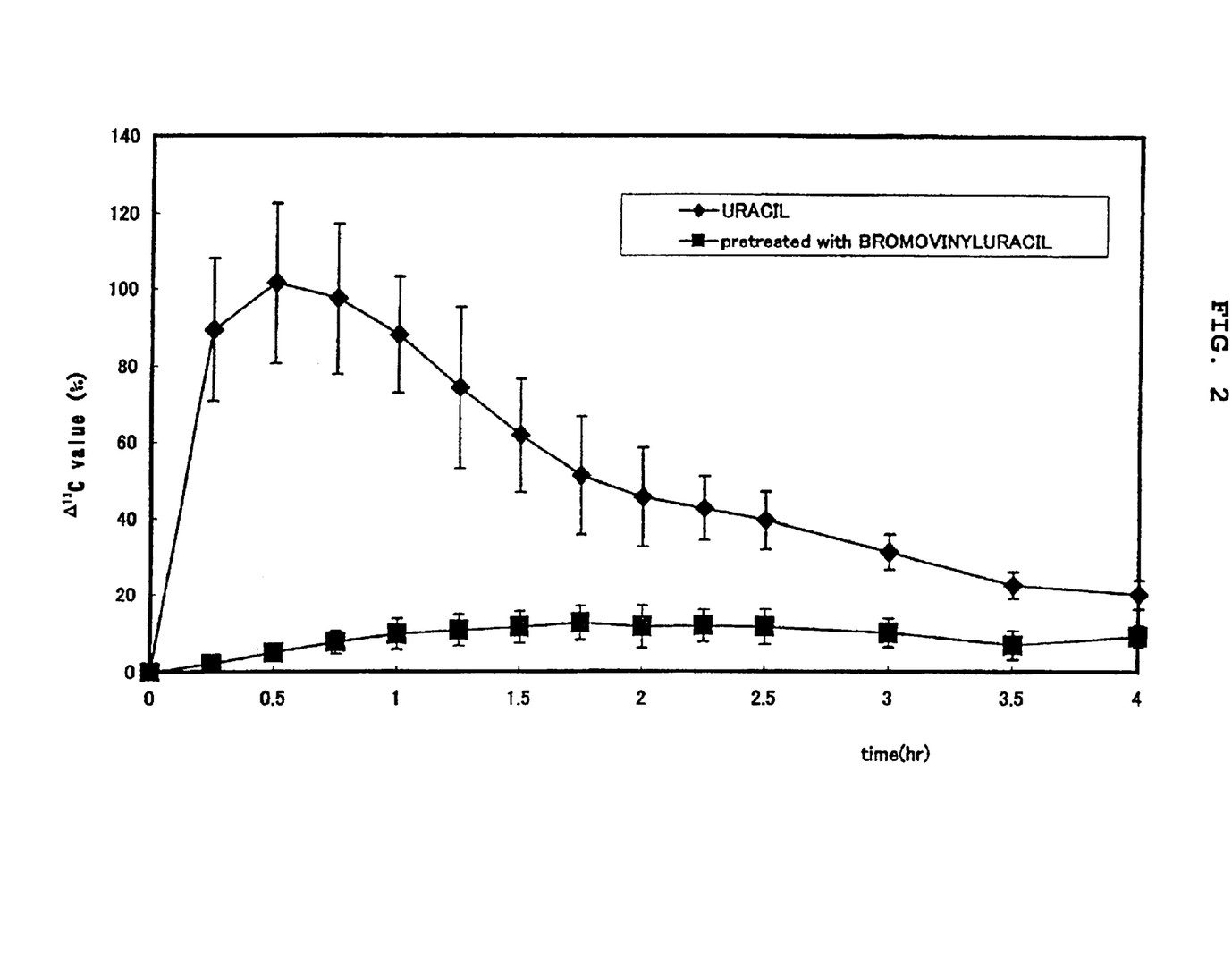
FIG. 2 shows the experiment results obtained in Example 1, in which the preparation of the invention was intravenously injected to experimental animals. In Example 1, after intravenous injection of uracil-2-$^{13}C$, behavior of $^{13}CO_2$ excreted in the expired air was observed over time in healthy animals (-♦-) and in model animals with uracil metabolic abnormality (-■-).

Fasted beagle dogs were used as experimental animals. In Group 1 (test group, n=3), the preparation for determining pyrimidine metabolizing activity was intravenously injected (50 mg/body). In Group 2 (comparative group: uracil metabolic abnormality animal models, n=3), the (E)-5-(2-bromovinyl)-uracil preparation was first administered orally (83.3 mg/body), and after 1 hour, the preparation for determining pyrimidine metabolizing activity was intravenously injected (50 mg/body) in the same manner as in Group 1. In both groups, the expired air was collected before administration of the preparation for determining pyrimidine metabolizing activity and 15, 30, 45, 60, 75, 90, 105, 120, 135, 150, 180, 210 and 240 minutes after administration of the preparation. The concentration of $^{13}C$-carbon dioxide excreted in the collected expired air was measured using a GC-MS analyzer (ABCA-G, Europa Scientific). FIG. 2 shows the results in the test group (-♦-) and those in the comparative group (-■-). In the figure, on the ordinate are plotted $\Delta^{13}C$ values (‰) which indicate the difference in $\delta^{13}C$ value (‰) ($^{13}CO_2/^{12}CO_2$ concentration ratio in the expired air) between the sample collected before administration of the preparation for determining pyrimidine metabolizing activity and each of the samples collected after administration of the preparation.

As is apparent from FIG. 2, it was observed that, in the test group, uracil-2-$^{13}C$ was metabolized and excreted in the expired air as $^{13}CO_2$. On the other hand, in the artificially created uracil metabolic abnormality animal models (comparative group), the excretion of $^{13}CO_2$ in the expired air was markedly lowered, indicating that uracil-2-$^{13}C$ was not properly metabolized and was retained in body.

Example 2

A preparation in an oral solution was prepared using the same uracil-2-$^{13}C$ as in Example 1 as an active ingredient, and tested for usefulness for measuring pyrimidine metabolizing activity.

(1) Preparation of a Preparation for Determining Pyrimidine Metabolizing Activity 300 mg of uracil-2-$^{13}C$ (Cambridge Isotope Laboratory) was dissolved in 24 ml of 0.1N NaOH/saline solution (measured out from 200 ml of 0.1N NaOH/saline solution prepared by diluting 2 ml of 10N sodium hydroxide solution with physiological saline). Then, water was added to give 60 ml of a preparation for determining pyrimidine metabolizing activity in the form of an oral solution (containing 50 mg of uracil-2-$^{13}$C per 10 ml of the oral solution).

(2) Experiment

Figure 3:
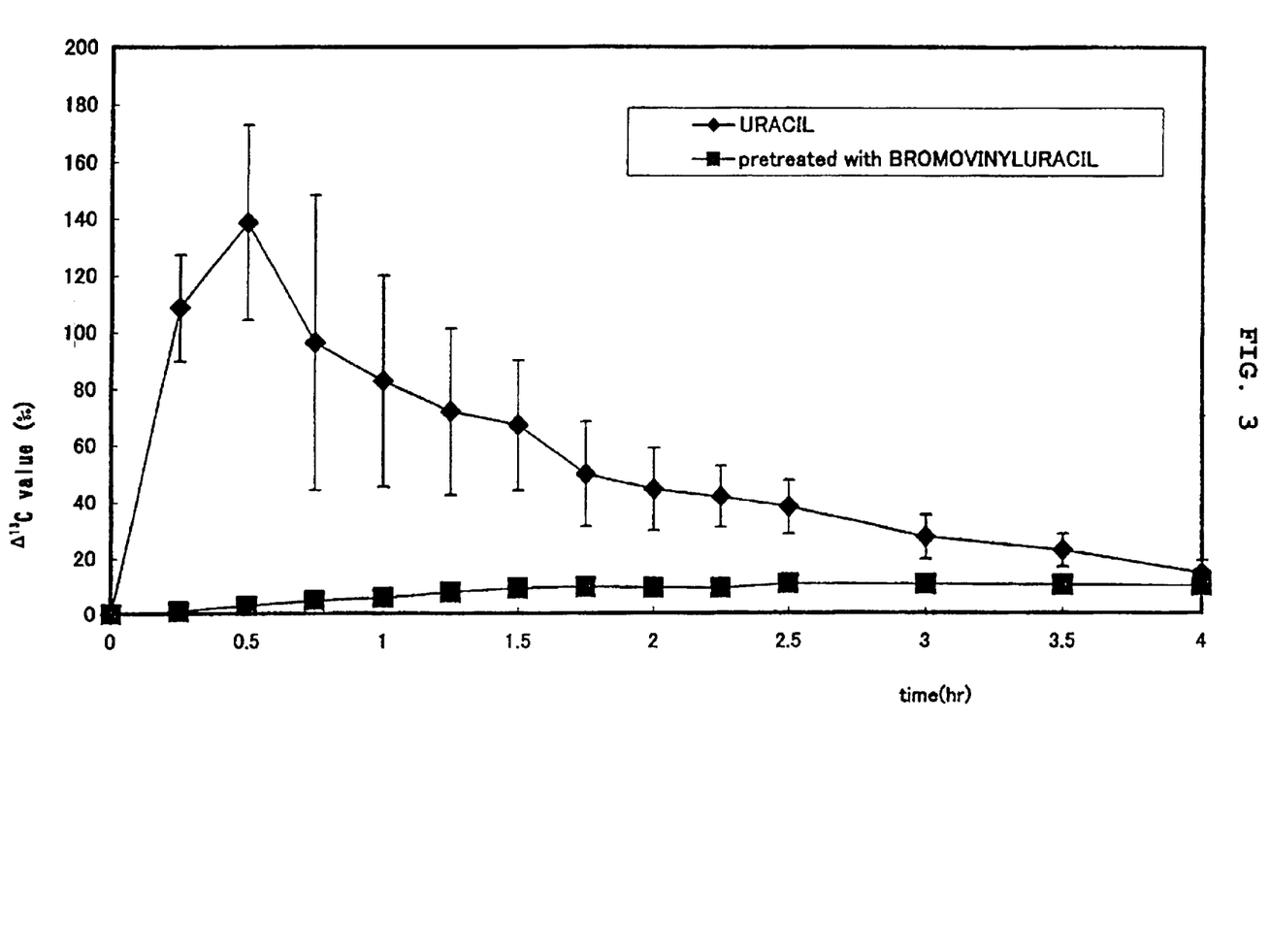
FIG. 3 shows the experiment results obtained in Example 2, in which the preparation of the invention is orally administered to experimental animals. In Example 2, after oral administration of uracil-2-$^{13}C$, behavior of $^{13}CO_2$ excreted in the expired air was observed over time in healthy animals (-♦-) and in model animals with uracil metabolic abnormality (-■-).

Fasted beagle dogs were used as experimental animals. In Group 1 (test group, n=3), the preparation prepared above in (1) was orally administered (50 mg/10 ml/body). In Group 2 (comparative group: uracil metabolic abnormality animal models, n=3), the (E)-5-(2-bromovinyl)uracil preparation prepared in the same manner as in Example 1-(2) was orally administered (83.3 mg/15 ml/body), and after 1 hours, the preparation for determining pyrimidine metabolizing activity was orally administered (50 mg/10 ml/body) in the same manner as in Group 1. In both groups, after oral administration of the preparation for determining pyrimidine metabolizing activity, 10 ml of water was forcibly administered orally using the tube used for administration of the preparation, to wash out the composition remaining in the tube. In both groups, the expired air was collected before administration of the preparation for determining pyrimidine metabolizing activity and 15, 30, 45, 60, 75, 90, 105, 120, 135, 150, 180, 210 and 240 minutes after administration of the preparation. The concentration of $^{13}$C-carbon dioxide excreted in the expired air was measured in the same manner as in Example 1, using a GC-MS analyzer (ABCA-G, Europa Scientific). FIG. 3 shows the results in the test group (-♦-) and those in the comparative group (-■-).

FIG. 3 reveals that the oral administration of the preparation of the invention achieves the similar results to the intravenous injection of the preparation (Example 1). Specifically, in the test group, uracil-2-$^{13}$C was metabolized and excreted in the expired air as $CO_2$, whereas in the artificially created uracil metabolic abnormality animal models (comparative group), the excretion of $^{13}CO_2$ in the expired air was markedly lowered, indicating that uracil-2-$^{13}$C was not properly metabolized and was retained in vivo. These results demonstrate that the preparation of the invention is useful for easy and precise determination of in vivo pyrimidine metabolizing activity using the expired air, regardless of its dosage form.

What is claimed is:

1. A method for determining pyrimidine metabolizing activity in an individual subject, comprising:
    (i) administering to the subject uracil or thymine wherein at least one of C, O, and N is labeled with a non-radioactive isotope, and measuring a non-radioactive isotope-labeled metabolite;
    (ii) administering to the subject dihydrouracil or dihydrothymine wherein at least one of C, O, and N is labeled with anon-radioactive isotope, and measuring a non-radioactive isotope-labeled metabolite;
    (iii) administering to the subject β-ureidopropionic acid or β-ureidoisobutyric acid wherein at least one of C, O, and N is labeled with a non-radioactive isotope, and measuring a non-radioactive isotope-labeled metabolite; and
    (iv) determining pyrimidine metabolizing activity in the subject from the measurements of Steps (i), (ii), and (iii).

2. A method, according to claim 1, wherein the non-radioactive isotope-labeled metabolite in (i), (ii), and (iii) is excreted from the body.

3. A method according to claim 2, wherein the non-radioactive isotope-labeled metabolite in (i), (ii), and (iii) is isotope-labeled $CO_2$, and the measuring comprises measuring the isotope-labeled $CO_2$ excreted as expired air.

4. A method according to claim 1, wherein the pyrimidine metabolizing activity to be determined is dihydropyrimidine dehydrogenase.

5. A method according to claim 1, wherein the measurement of the non-radioactive isotope-labeled metabolite from the subject in (i), (ii), and (iii) is compared with the measurement from a healthy subject.

6. A method according to claim 2, wherein the measurement of the non-radioactive isotope-labeled metabolite from the subject in (i), (ii), and (iii) is compared with the measurement from a healthy subject.

7. A method according to claim 3, wherein the measurement of the non-radioactive isotope-labeled metabolite from the subject in (i), ii), and (iii) is compared with the measurement from a healthy subject.

8. A method for determining a dosage regimen of a pyrimidine drug, comprising:
    administering to the subject a preparation comprising a pyrimidine compound or its metabolite wherein at least one of C and O is labeled with a non-radioactive isotope $^{13}$C and $^{18}$O, respectively;
    measuring a non-radioactive isotope-labeled $CO_2$ excreted as expired air to assess pyrimidine metabolizing activity in the subject; and
    determining the dosage regimen based on the assessed pyrimidine metabolizing activity.

9. A method according to claim 8, wherein the pyrimidine drug is a fluorouracil drug selected from 5-fluorouracil, tegafur, carmofur and doxifluridine.

10. The method according to claim 8, wherein the pyrimidine metabolizing activity to be determined is an activity of at least one pyrimidine metabolizing enzyme selected from dihydropyrimidine dehydrogenase, dihydropyrimidinase and β-ureidopropionase.

11. The method according to claim 1, wherein at least one of C and O is labeled with $^{13}$C and $^{18}$O, respectively.

12. A method for determining pyrimidine metabolizing activity in an individual subject, comprising:
    (i) administering to the subject dihydrouracil or dihydrothymine wherein at least one of C, O, and N is labeled with a non-radioactive isotope, and measuring a non-radioactive isotope-labeled metabolite;
    (ii) administering to the subject β-ureidopropionic acid, β-ureidoisobutyric acid wherein at least one of C, O, and N is labeled with a non-radioactive isotope, and measuring a non-radioactive isotope-labeled metabolite; and
    (iii) determining pyrimidine metabolizing activity in the subject from the measurements of steps (i) and (ii).

13. A method according to claim 12, wherein the non-radioactive isotope-labeled metabolite in (i) and (ii) is excreted from the body.

14. A method according to claim 13, wherein the non-radioactive isotope-labeled metabolite in (i) and (ii) is isotope-labeled $CO_2$, and the measuring comprises measuring the isotope-labeled $CO_2$ excreted as expired air.

15. A method according to claim 12, wherein the pyrimidine metabolizing activity to be determined is dihydropyrimidinase.

16. A method according to claim 12, wherein the pyrimidine metabolizing activity to be determined is B-ureidopropiohase.

17. A method according to claim 12, wherein the measurement of the non-radioactive isotope-labeled metabolite from the subject in (i) and (ii) is compared with the measurement from a healthy subject.

18. A method according to claim 13, wherein the measurement of the non-radioactive isotope-labeled metabolite from the subject (i) and (ii) is compared with the measurement from a healthy subject.

19. A method according to claim 14, wherein the measurement of the non-radioactive isotope-labeled metabolite from the subject (i) and (ii) is compared with the measurement from a healthy subject.

20. The method according to claim 12, wherein at least one of C and O is labeled with $^{13}$C and $^{18}$O, respectively.

* * * * *